US009084897B2

(12) United States Patent
Yonce

(10) Patent No.: US 9,084,897 B2
(45) Date of Patent: Jul. 21, 2015

(54) TIBIAL NERVE STIMULATION THERAPY DEVICE CALIBRATION

(71) Applicant: AMS Research Corporation, Minnetonka, MN (US)

(72) Inventor: David J. Yonce, Edina, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 14/085,320

(22) Filed: Nov. 20, 2013

(65) Prior Publication Data
US 2014/0142662 A1 May 22, 2014

Related U.S. Application Data

(60) Provisional application No. 61/728,621, filed on Nov. 20, 2012.

(51) Int. Cl.
*A61N 1/00* (2006.01)
*A61N 1/36* (2006.01)

(52) U.S. Cl.
CPC .......... *A61N 1/36139* (2013.01); *A61N 1/3606* (2013.01); *A61N 1/36185* (2013.01); *A61N 1/36071* (2013.01)

(58) Field of Classification Search
CPC .................................................. A61N 1/3605
USPC ............................................... 607/41, 45, 46
See application file for complete search history.

(56) References Cited

U.S. PATENT DOCUMENTS 6,735,474 B1   5/2004   Loeb et al.
6,937,891 B2   8/2005   Leinders et al.
(Continued)

FOREIGN PATENT DOCUMENTS

GB        1392439 A      4/1975
WO     2010019867 A1    2/2010
(Continued)

OTHER PUBLICATIONS

International Search Report and Written Opinion dated Jan. 18, 2013 for International Patent Application No. PCT/US2012/060363, filed Oct. 16, 2013.
(Continued)

*Primary Examiner* — Christopher D Koharski
*Assistant Examiner* — Nadia A Mahmood
(74) *Attorney, Agent, or Firm* — Westman, Champlin & Koehler, P.A.

(57) ABSTRACT

A tibial nerve stimulation therapy device configured to provide an electrical stimulation therapy to branches of the tibial nerve includes a plurality of stimulation electrodes, a stimulation circuit configured to generate electrical stimulation pulses, a sensing circuit configured to generate an output signal indicative of an electromyogram (EMG) signal generated by the patient, and a controller. The controller is configured to execute a plurality of unique stimulation therapies in accordance with unique stimulation therapy settings, analyze the output signals generated by the sensing circuit after each of the stimulation therapies, and designate final stimulation therapy settings based on the analyzed output signals. The stimulation therapy settings include an identification of a pair of the electrodes through which the electrical stimulation pulses are delivered during a stimulation therapy, and/or at least one parameter defining the electrical stimulation pulses generated by the stimulation circuit.

19 Claims, 8 Drawing Sheets

(56) References Cited

U.S. PATENT DOCUMENTS

| | | |
|---|---|---|
| 7,415,308 B2 | 8/2008 | Gerber et al. |
| 7,590,453 B2 | 9/2009 | Heruth et al. |
| 2005/0222635 A1 | 10/2005 | Krakovsky |
| 2006/0161219 A1 | 7/2006 | Mock et al. |
| 2006/0195145 A1 | 8/2006 | Lee et al. |
| 2006/0229687 A1* | 10/2006 | Goetz et al. ............ 607/46 |
| 2007/0179559 A1 | 8/2007 | Giftakis et al. |
| 2007/0253997 A1 | 11/2007 | Giftakis et al. |
| 2007/0253998 A1 | 11/2007 | Giftakis et al. |
| 2007/0255333 A1 | 11/2007 | Giftakis et al. |
| 2007/0255341 A1 | 11/2007 | Giftakis et al. |
| 2008/0103574 A1 | 5/2008 | Gerber |
| 2009/0054952 A1 | 2/2009 | Glukhovsky et al. |
| 2009/0082835 A1 | 3/2009 | Jaax et al. |
| 2009/0326602 A1 | 12/2009 | Glukhovsky et al. |
| 2010/0106231 A1 | 4/2010 | Torgerson et al. |
| 2011/0301670 A1* | 12/2011 | Gross et al. ............ 607/62 |

FOREIGN PATENT DOCUMENTS

| | | |
|---|---|---|
| WO | 2011100162 A1 | 8/2011 |
| WO | 2013034599 A1 | 3/2013 |
| WO | 2013059158 A1 | 4/2013 |

OTHER PUBLICATIONS

International Search Report and Written Opinion dated Nov. 19, 2012 for International Patent Application No. PCT/US2012/053903, filed Sep. 6, 2012.

U.S. Appl. No. 61/549,310, filed Oct. 20, 2011.

U.S. Appl. No. 61/532,744, filed Sep. 9, 2011.

International Search Report and Written Opinion for PCT/US2011/023677, mailed Apr. 21, 2011.

U.S. Appl. No. 61/734,070, filed Dec. 6, 2012.

International Search Report and Written Opinion for PCT/US2012/053903, mailed Nov. 19, 2012.

EPO Communication for European Patent Application No. 12784154.2, dated Jul. 3, 2014.

EPO Communication for European Patent Application No. 12762135.7, dated May 9, 2014.

\* cited by examiner

TIBIAL NERVE STIMULATION THERAPY DEVICE CALIBRATION

CROSS-REFERENCE TO RELATED APPLICATION

This application claims the benefit of U.S. Provisional Application No. 61/728,621 filed Nov. 20, 2012, which is hereby incorporated by reference in its entirety.

FIELD

Embodiments of the invention are directed to a stimulation therapy device and method for stimulating branches of nerves in the tibial area of a patient. This stimulation can be used to treat a pelvic condition of a patient, such as overactive bladder or urge incontinence, for example.

BACKGROUND

The tibial nerve is a branch of the sciatic nerve that passes alongside the tibia and into the foot. At the ankle, the tibial nerve is relatively close to the surface of the skin. Stimulation of the tibial nerve can be used to treat urinary incontinence, fecal incontinence, pelvic pain, and other conditions.

These stimulation treatments typically involve the use of a percutaneous electrode or device that is inserted into the subject's ankle. For instance, U.S. Pat. No. 6,735,474 (Loeb et al.) discloses the use of micro-stimulators that are inserted beneath the skin of the perineum and/or adjacent the tibial nerve to treat incontinence, pelvic pain, and fecal incontinence. U.S. Publication No. 2011/0301670 (Gross et al.) discloses the use of percutaneous electrodes that are placed in contact with the tibial nerve to deliver electrical stimulation signals to the nerve to treat polyneuropathy. Uroplasty Inc. (Minnesota, USA) manufactures the Urgent® PC Neuromodulation System, which delivers electrical stimulation to the tibial nerve using a percutaneous needle electrode to treat urinary urgency, urinary frequency (i.e., overactive bladder), and urge incontinence.

SUMMARY

Embodiments of the invention relate to a tibial nerve stimulation therapy device configured to provide an electrical stimulation therapy to branches of the tibial nerve of a patient, and methods of calibrating the tibial nerve stimulation device. In some embodiments, the device includes a plurality of stimulation electrodes, a stimulation circuit, a sensing circuit, and a controller. The stimulation circuit is configured to generate electrical stimulation pulses. The sensing circuit is configured to generate an output signal indicative of an electromyogram (EMG) signal generated by the patient. The controller includes a processor and is configured to execute a plurality of unique stimulation therapies, during which an electrical stimulation pulse is delivered through a pair of the electrodes. Each stimulation therapy is performed in accordance with unique stimulation therapy settings. The controller is also configured to analyze the output signals generated by the sensing circuit after each of the stimulation therapies, and designate final stimulation therapy settings based on the analyzed output signals. The stimulation therapy settings include an identification of a pair of the electrodes through which the electrical stimulation pulses are delivered during a stimulation therapy, and/or at least one parameter defining the electrical stimulation pulses generated by the stimulation circuit.

In some embodiments of the method, multiple unique stimulation therapies are performed on a patient using the device. Each stimulation therapy includes steps of: generating an electrical stimulation pulse using the stimulation circuit; delivering the electrical stimulation pulse to the tibial nerve of the patient through a candidate pair of the stimulation electrodes; and sensing an electromyogram (EMG) signal generated by the patient responsive to the delivering step, and generating an output signal indicative of the EMG signal, using the sensing circuit. Also in the method, the output signals generated by the sensing circuit are analyzed using the controller. The stimulation therapy settings or subsequent stimulation therapies have been designated based on the analysis performed by the controller.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION OF ILLUSTRATIVE EMBODIMENTS

Figure 1:
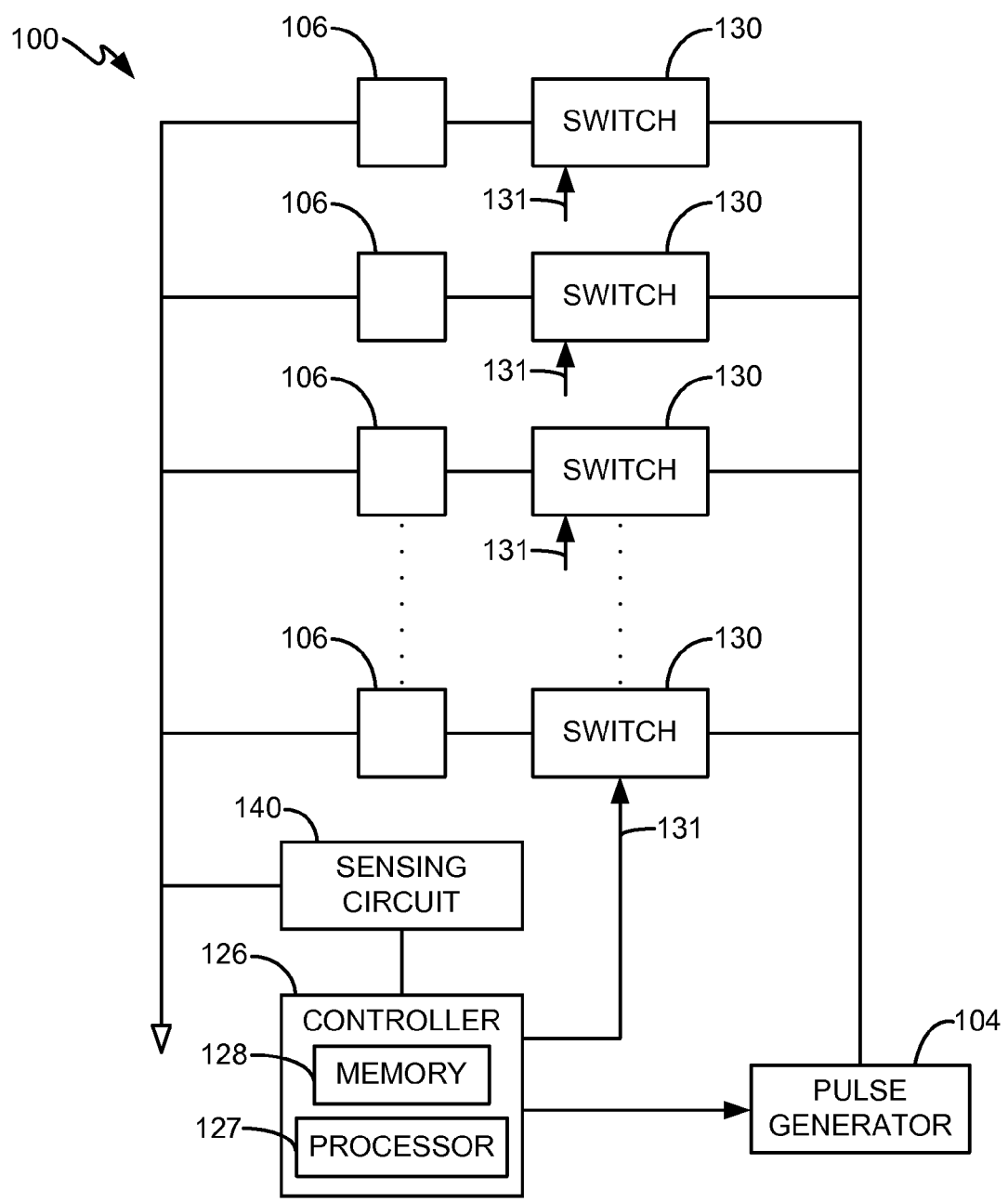
FIG. 1 is a block diagram of a tibial nerve stimulation therapy device 100 in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As will further be appreciated by one of skill in the art, the present invention may be embodied as methods, systems, and/or computer program products. Accordingly, the present invention may take the form of an entirely hardware embodiment, an entirely software embodiment or an embodiment combining software and hardware aspects. Furthermore, the present invention may take the form of a computer program product on a computer-usable storage medium or memory having computer-usable program code embodied in the medium. Any suitable computer readable medium may be utilized including hard disks, CD-ROMs, optical storage devices, magnetic storage devices.

The computer-usable or computer-readable medium or memory may be, for example but not limited to, an electronic, magnetic, optical, electromagnetic, infrared, or semiconductor system, apparatus, device, or propagation medium. Such computer readable media and memory for computer programs and software do not include transitory waves or signals. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The invention is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

Accordingly, the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

Figure 2:
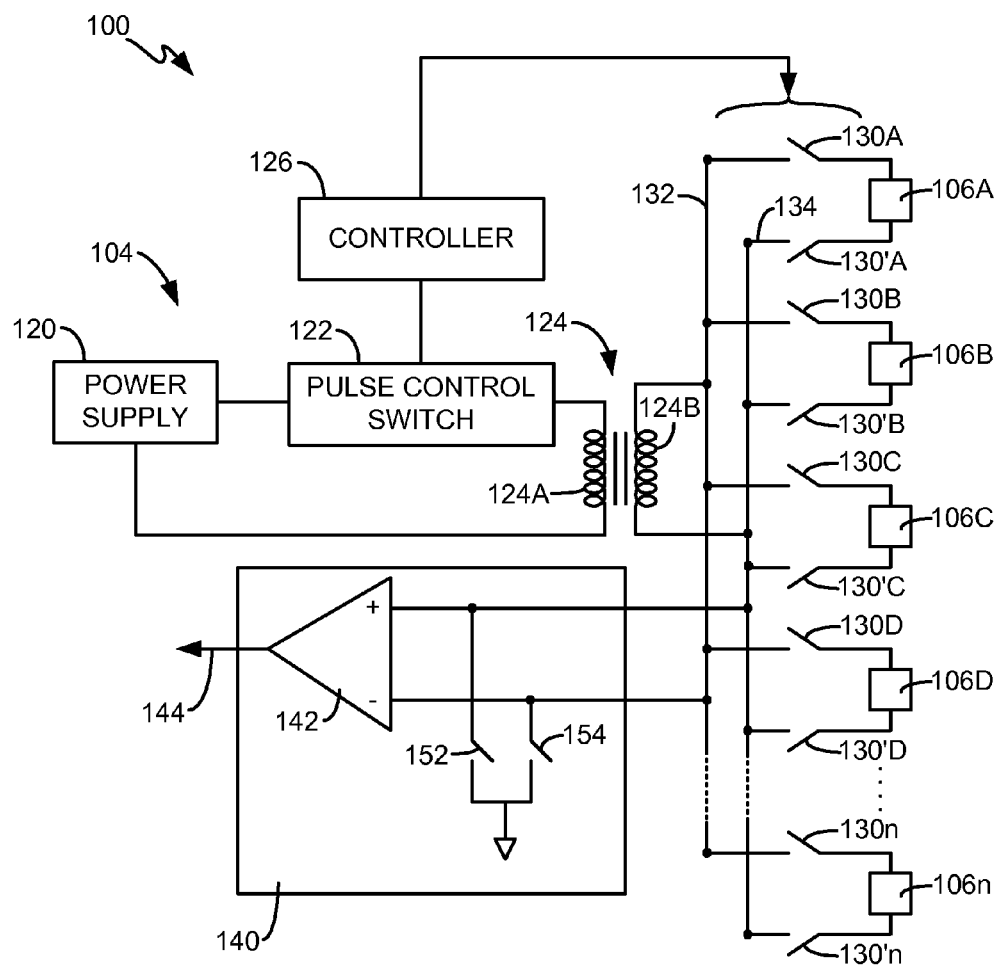
FIG. 2 is a simplified circuit diagram of an exemplary tibial nerve stimulation therapy device in accordance with embodiments of the invention.
Figure 3:
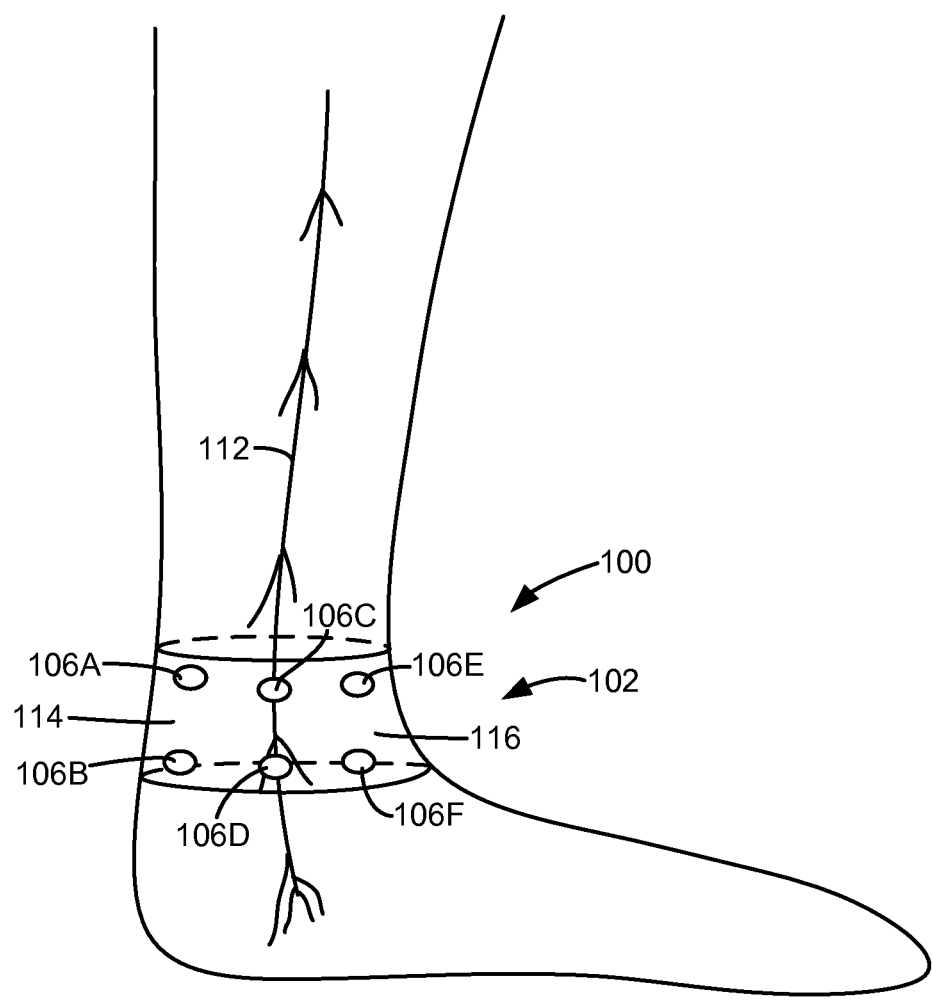
FIG. 3 is a simplified diagram of a tibial nerve stimulation therapy device, or a portion thereof, supported around an ankle area of a patient, in accordance with embodiments of the invention.

FIG. 1 is a block diagram of a tibial nerve stimulation therapy device 100, and FIG. 2 is a simplified circuit diagram of an exemplary device 100, in accordance with embodiments of the invention. FIG. 3 is a simplified diagram of the device 100, or a portion thereof, supported around an ankle area 102 of a patient. As used herein the "ankle area" refers to the ankle and the foot of the patient. Accordingly, as used herein, embodiments describing attaching or positioning electrodes to the ankle area of a patient include attaching or positioning electrodes on the foot of the patient.

In some embodiments, the device 100 includes a stimulation circuit or pulse generator 104 and one or more electrodes 106. Embodiments of the electrodes 106 include transcutaneous surface or patch electrodes that engage the skin of the ankle area 102. In some embodiments, the surface electrodes spread the stimulation pulses over a wide physical area to maximize the spread of the electrical field potentials and increase the chance of stimulating the nerve or muscle. In some embodiments, the electrical pulses delivered to the ankle area 102 through the one or more electrodes 106 are at least partially conducted through one or more branches of the tibial nerve 112. In some embodiments, this application of the electrical stimulation pulses to the tibial nerve 112 treats a pelvic condition of the patient, such as those mentioned above.

In some embodiments, the device 100 includes a plurality of electrodes 106, such as electrodes 106A, 106B, 106D, as shown in FIGS. 1-3. In some embodiments, the electrodes 106 are displaced from each other around the ankle area 102. In some embodiments, the device 100 supports the electrodes 106 in a vertical arrangement such that they are oriented with the tibial nerve 112 (FIG. 2) of the patient and are configured to stimulate along the length of the tibial nerve 112. Note that while the drawing shows pairs of electrodes, such as electrodes 106A and 106B, placed in this fashion, more than two electrodes 106 may be situated along the length of the leg and tibial nerve 112 as well.

In some embodiments, the device 100 includes a support member 114 that positions the electrodes 106 in the desired locations on the ankle area 102 of the patient, as shown in FIG. 3. In some embodiments, each of the electrodes 106 includes a stimulation surface that faces away from a stimulation side of the support member 114 and through which the current pulses are conducted to the patient. In some embodiments, the support member 114 comprises straps 116 that attach to each other to secure the device 100 to the ankle area of the patient. In some embodiments, the support member 114 is in the form of an ankle bracelet. In accordance with another embodiment, the support member 114 comprises a sock-like member that is worn by the patient.

In some embodiments, the stimulation circuit 104 is configured to generate direct current electrical pulses or stimulation signals that are delivered to the tibial nerve 112 through the electrodes 106 to perform a desired stimulation therapy on the patient. In some embodiments, the stimulation circuit 104 comprises a power supply 120, a pulse control switch 122, and a transformer 124. In some embodiments, the power supply 120 includes a battery (e.g., 3 volt battery) or other suitable power supply. In some embodiments, the transformer 124 is a step-up transformer having a primary winding 124A and a secondary winding 124B. The transformer 124 increases the primary voltage supplied to the primary winding 124A from the power supply 120 through line 131 to a secondary voltage at the secondary winding 124B that is coupled to the one or more electrodes 106. In one embodiment, the primary voltage is approximately 3 volts and the secondary voltage is approximately 20-120V. In more specific embodiments, the secondary voltage is 20V or 30V. Other primary and secondary voltages may also be used.

Note that while FIG. 1 shows a configuration with a single transformer and switches connected to the secondary coil 124B, multiple transformers could be used and the switches could instead be connected on the primary side 124A. Additionally, the circuit 104 could be constructed in a topology that does not use a transformer.

In some embodiments, a controller 126 includes at least one processor 127 that is configured to execute program instructions stored in memory 128 of the controller 126, or other location, to execute functions described herein, in accordance with conventional techniques.

In some embodiments, the controller 126 is configured to control the generation of the stimulation pulses by the stimulation circuit 104 by controlling the flow of the current from the power supply 120 to the transformer 124 using the pulse control switch 122. The controller 126 opens the pulse control switch 122 to prevent current from flowing through the transformer 124, and closes the pulse control switch 122 to deliver current through the transformer 124. The flow of current through the transformer 124 produces a current flow or pulses through the selected electrodes 106 when placed in contact with the ankle area 102 of the patient, as shown in FIG. 3. Embodiments of the pulse control switch 122 include a transistor or other suitable electrical component or circuit. Thus, a duty cycle of the stimulation pulses is controlled by regulating the pulse width of the primary side of the step-up transformer 124 by actuating the pulse control switch 122 using the controller 126.

As mentioned above, embodiments of the device 100 operate to deliver electrical stimulation pulses generated by the stimulation circuit 104 to one or more of the electrodes 106 (i.e., a subset of the electrodes 106). In some embodiments, the circuit 104 includes a plurality of pulse routing switches 130 (e.g., transistors) that are selectively opened or closed in response to control signals 131 from the controller 126 to selectively couple a subset of the electrodes 106 to the electrical stimulation pulses generated by the stimulation circuit 104, as shown in FIG. 1. In some embodiments, a plurality of the pulse routing switches 130 are configured to electrically couple and decouple each of the electrodes 106 to line 132 of the secondary winding 124B, such as switches 130A-130n, as shown in FIG. 2. In some embodiments, the pulse routing switches 130 include a plurality of switches 130', such as 130A'-n', that are configured to electrically couple and decouple each of the electrodes 106 to line 132 of the secondary winding 124B, as shown in FIG. 2. In some embodiments, the signals 131 produced by the controller 126 controls the actuation of the switches 130 between open and closed positions to respectively couple and decouple the corresponding electrodes 160 to lines 132 or 134, and control the delivery of the stimulation current or pulses to a subset of the electrodes 106.

In some embodiments, the circuit 104 includes a sensing circuit 140 that is configured to sense an electromyogram (EMG) signal generated by the patient in response to the application of a stimulation therapy (i.e., electrical stimulation pulses) to the tibial nerve 112 through a sense electrode. In some embodiments, the sense electrode comprises one or more of the electrodes 106. In some embodiments, a sense electrode is placed on the foot of the patient for better sensing of the associated EMG signal. In some embodiments, the sense electrode is supported by the support member 114.

In some embodiments, the sensing circuit 140 includes a sensing amplifier 142 that is coupled to the lines 132 and 134, or one or more of the electrodes 106, as shown in FIG. 2. In some embodiments, switches (not shown) are in line with the sensing amplifier 142, and are controlled by the controller 126 to either couple or decouple the sensing circuit 140 to the lines 132 and 134, or one or more of the electrodes 106. As a result, one or more of the electrodes 106 may be used as a sensing channel to record an EMG signal. In one embodiment, the one or more electrodes 106 used to sense the EMG signal are not the electrodes used to apply the stimulation pulses to the patient. The amplified EMG output signal 144 from the amplifier 142 indicates the effectiveness of the stimulation therapy.

Figure 4:
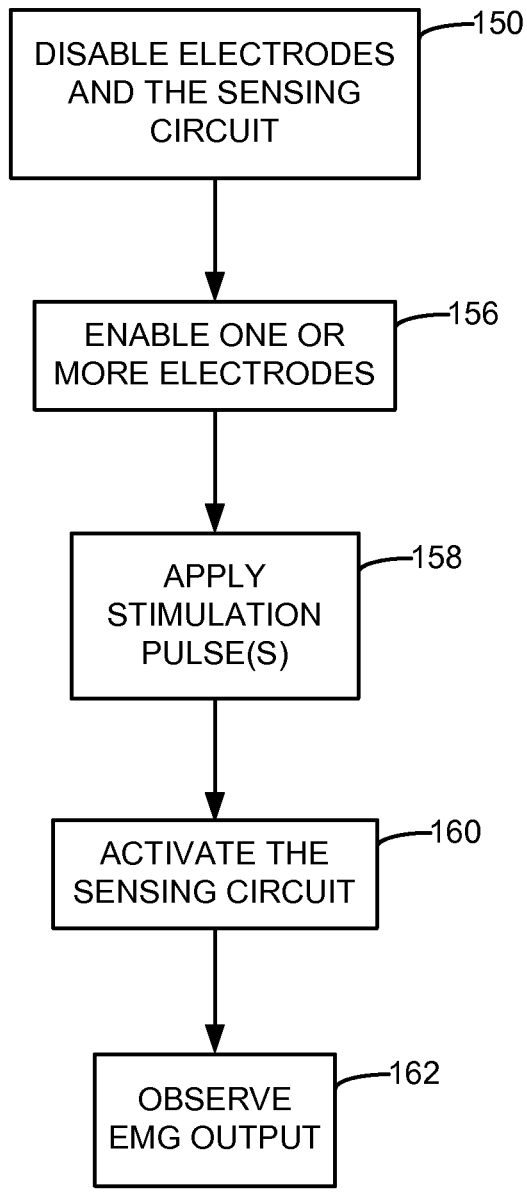
FIG. 4 is a flowchart illustrating operation of a tibial nerve stimulation therapy device in accordance with embodiments of the invention.

FIG. 4 is a flowchart illustrating the device 100 in operation. In some embodiments, the EMG sensing occurs immediately following the execution of a stimulation therapy, during which stimulation pulses are delivered through the one or more electrodes 106. In some embodiments, the electrodes 106 and the sensing circuit 140 are disabled, as indicated at 150, prior to commencing a stimulation therapy. This may be accomplished by opening the switches 106, and driving the inputs to the amplifier 142 to ground through switches 152 and 154, or disconnecting the amplifier 142 from the lines 132 and 134 or the electrodes 106 using an appropriate switch, for example.

At 156, one or more of the electrodes 106 are enabled or activated. In some embodiments, the electrodes 106 are enabled by the controller 126 through the closing of one or more of the switches 130. At 158, stimulation pulses are delivered to the patient through the enabled electrodes 106. At 160, the sensing circuit 140 is activated and the EMG signal generated by the patient in response to the stimulation pulses is analyzed by the controller 126, or other control unit, through analysis of the EMG output signal 144, at 162.

Some embodiments of the invention are directed to a calibration routine for the device 100 that can automatically determine stimulation therapy settings for the device 100 that effectively stimulate the tibial nerve of the patient. In some embodiments, the calibration routine determines stimulation settings for the device that minimize patient discomfort and preserve battery power. In some embodiments, the stimulation therapy settings include an identification of a pair of the electrodes 106 that will receive the electrical stimulation pulses from the stimulation circuit 104 during a stimulation therapy, and/or at least one parameter defining the electrical stimulation pulses generated by the stimulation circuit 104, such as a power level (e.g., duty cycle, pulse width, voltage level, current level, etc.) for the electrical stimulation pulses.

Figure 5:
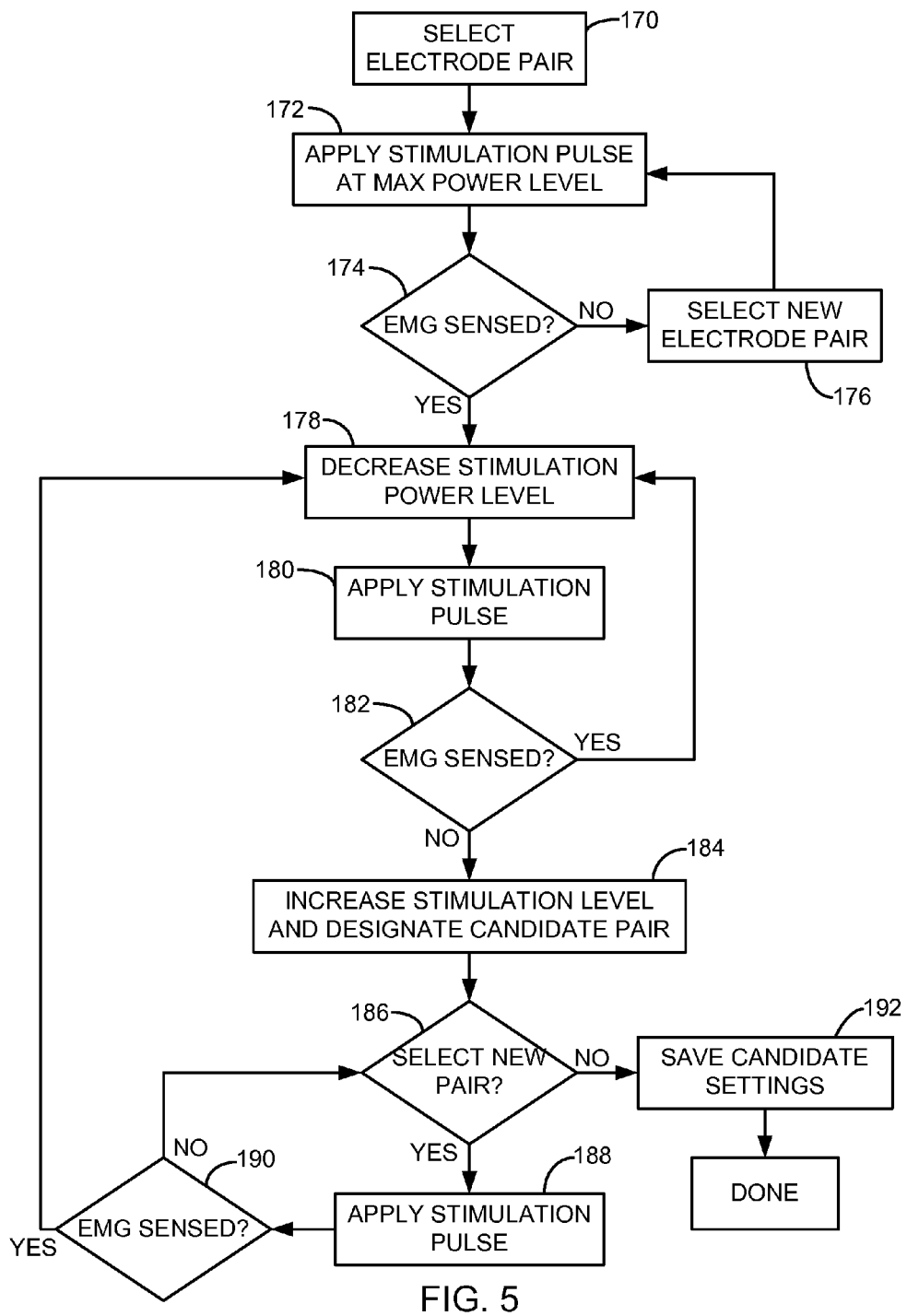
FIG. 5 is a flowchart illustrating a calibration routine for a tibial nerve stimulation therapy device in accordance with embodiments of the invention.

FIG. 5 is a flowchart illustrating a calibration routine for the device 100 in accordance with embodiments of the invention that is performed using the controller 126. In some embodiments, the calibration routine finds the pair of electrodes 106 that are most effective at applying the stimulation pulses to the tibial nerve 112 and optimizes the stimulation level. The stimulation therapy settings are then set to identify the found pair of electrodes 106 and/or set the one or more parameters of the stimulation pulses in accordance with the optimized stimulation level.

Initially, candidate stimulation therapy settings are designated using the controller 126 that include an identification of a candidate pair of the electrodes 106, which are selected at 170. The candidate pair of electrodes 106 are enabled by the controller 126 through the closing of one or more of the switches 130. At 172, a stimulation pulse is applied at a maximum or other preset high power level based on a candidate stimulation pulse parameter. At 174, the EMG response from the patient is sensed, such as using the sensing circuit 140, and analyzed by the controller 126. If the controller 126 determines that an EMG response from the patient is not sensed or does not meet a threshold requirement at 174, the candidate settings are adjusted by selecting a new candidate pair of electrodes 106 using the controller 126, as indicated at 176. The method returns to step 172 where a stimulation pulse is applied to the patient through the newly selected pair of electrodes 106. If the controller 126 determines that the output signal 144 indicates that a sufficient EMG response was generated by the patient at step 174, the calibration routine moves to 178 where the controller 126 decreases the candidate stimulation power level by a predetermined unit amount.

At 180, a stimulation pulse in accordance with the new candidate settings is applied to the patient through the candidate pair of electrodes 106. At 182, the controller 126 determines whether the output signal 144 from the sensing circuit 140 indicates that an EMG signal produced by the patient in response to the stimulation pulse is sensed by the device 100. If the controller 126 determines that a sufficient EMG signal is sensed by the device 100, the calibration routine returns to step 178 where the candidate stimulation power level is decreased by another unit. If the controller 126 determines that a sufficient EMG signal is not sensed by the device 100 at 182, the stimulation power level is increased by a unit to the last known power level at which an EMG signal is sensed by the device 100, and the currently enabled candidate pair of electrodes 106 are designated as a final candidate pair of electrodes 106.

At 186, a new pair of the electrodes 106 is selected as candidate pair of electrodes 106, which are enabled by the controller 126 for delivering a stimulation pulse to the patient. At 188, a stimulation pulse is applied to the patient through the selected new pair of electrodes 106, and the device 100 attempts to sense an EMG signal from the patient in response to the stimulation at 190, using the sensing circuit 140. If the EMG signal is sensed by the device 100, the calibration routine returns to 178 and continues as described above. If the EMG signal is not sensed by the device 100, the calibration routine returns to step 186.

If all of the electrode pairs 106 have been selected, the calibration routine moves to 192 and the candidate electrode pair and candidate pulse power level are saved as the stimulation therapy settings to complete the calibration of the device 100. In some embodiments, stimulation therapy settings identify the current candidate pair of electrodes 106 as the electrodes 106 that will be used to apply subsequent stimulation therapies to the patient. In one embodiment, the settings also include the power level for the candidate pair of electrodes 106 set at step 184.

Figure 6:
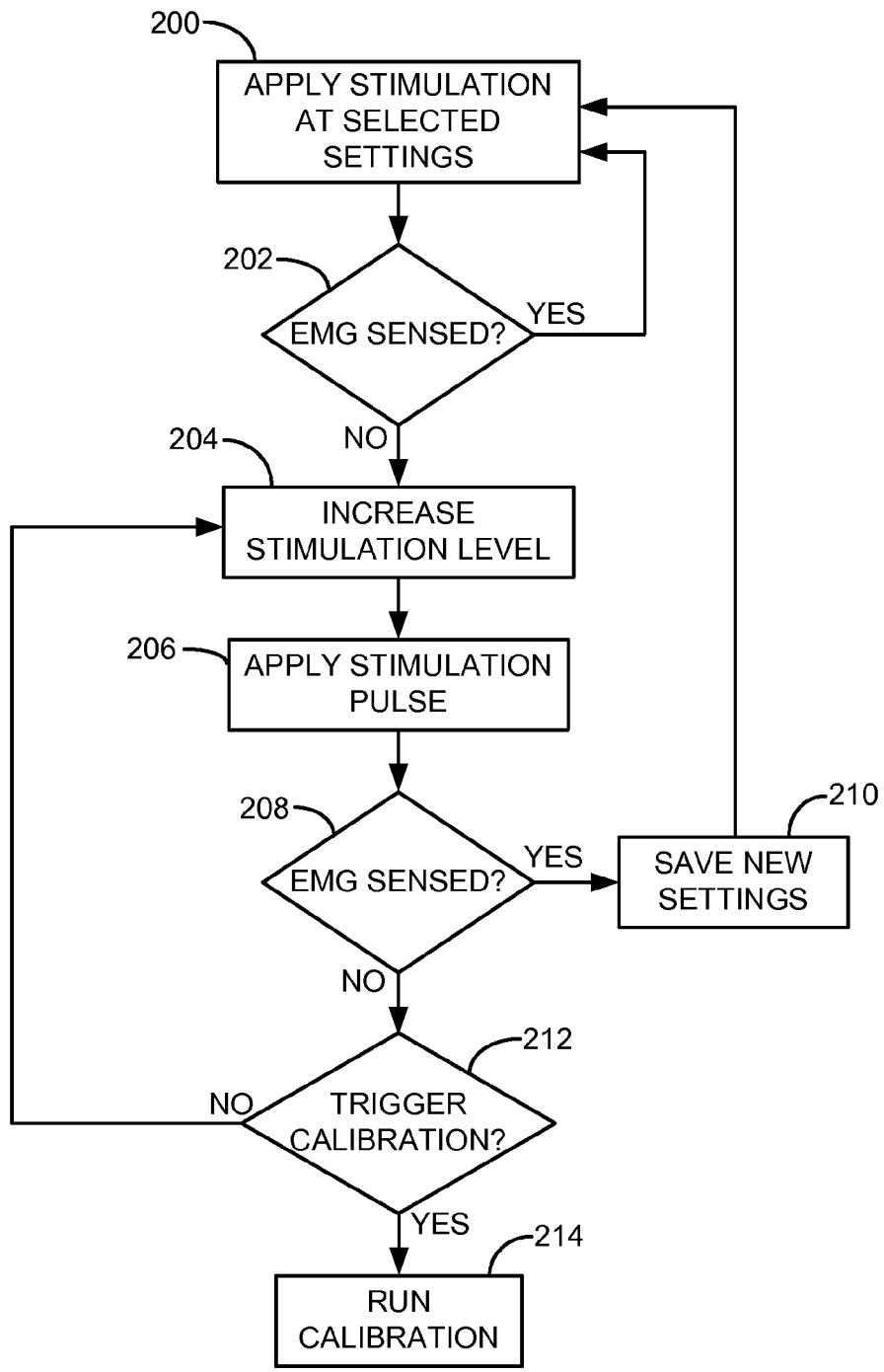
FIG. 6 is a flowchart illustrating a method of operating a tibial nerve stimulation therapy device in accordance with embodiments of the invention.

Once the pair of electrodes and the stimulation level has been optimized, the system can also function on a pulse-to-pulse basis to ensure continuity of stimulation throughout the therapy cycle, as shown in the flowchart of FIG. 6. During a stimulation therapy, stimulation pulses are applied to the patient at selected settings, as indicated at 200. These settings include the one or more electrodes 106 that are enabled to deliver the stimulation pulses to the patient, and the power level of the stimulation pulses, for example. At 202 of the method, the device 100 determines whether an EMG signal from the patient is sensed, such as using the sensing circuit 140 and the controller 126. If the controller 126 determines that a sufficient EMG signal is sensed by the device 100, the stimulation therapy continues by returning to 200. If the controller 126 determines that a sufficient EMG signal is not sensed by the device 100, the method moves to 204 where the stimulation power level is increased by a predetermined amount, and stimulation pulses at the new power level are applied to the patient at 206.

At 208, the controller 126 determines whether a sufficient EMG signal is sensed by the device 100 in response to the stimulation pulse or pulses applied at 206. If the EMG is sensed, the method moves to 210 where the current settings for the stimulation therapy are saved and the method moves back to 200 where stimulation pulses are applied to the patient a limited number of times in accordance with the stimulation therapy.

If the controller 126 determines that a sufficient EMG signal is not sensed at 208, the method moves to 212 where a determination is made as to whether the device 100 requires calibration. In some embodiments, this generally involves determining whether the stimulation power level has reached a threshold maximum where an additional increase in the power level of the stimulation pulses is not possible or is undesired. If the threshold is not reached at 212, the method returns to 204. If it is determined at 212 that a device calibration is required, the method moves to 214 where the calibration routine is run on the device 100. In some embodiments, the calibration routine involves that described above with regard to FIG. 5.

Figure 7:
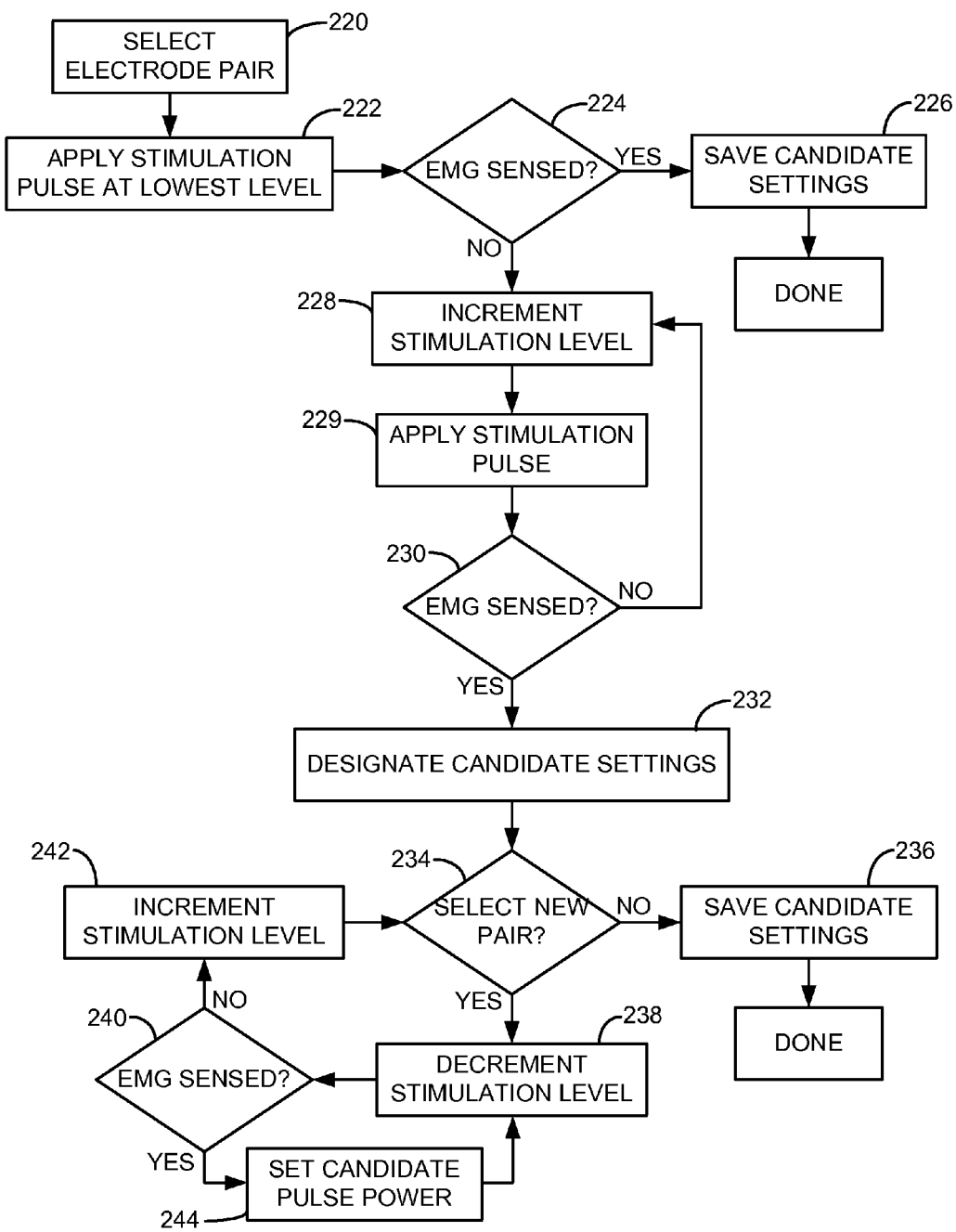
FIGS. 7 and 8 are flowcharts illustrating calibration routines for a tibial nerve stimulation therapy device in accordance with embodiments of the invention.
Figure 8:
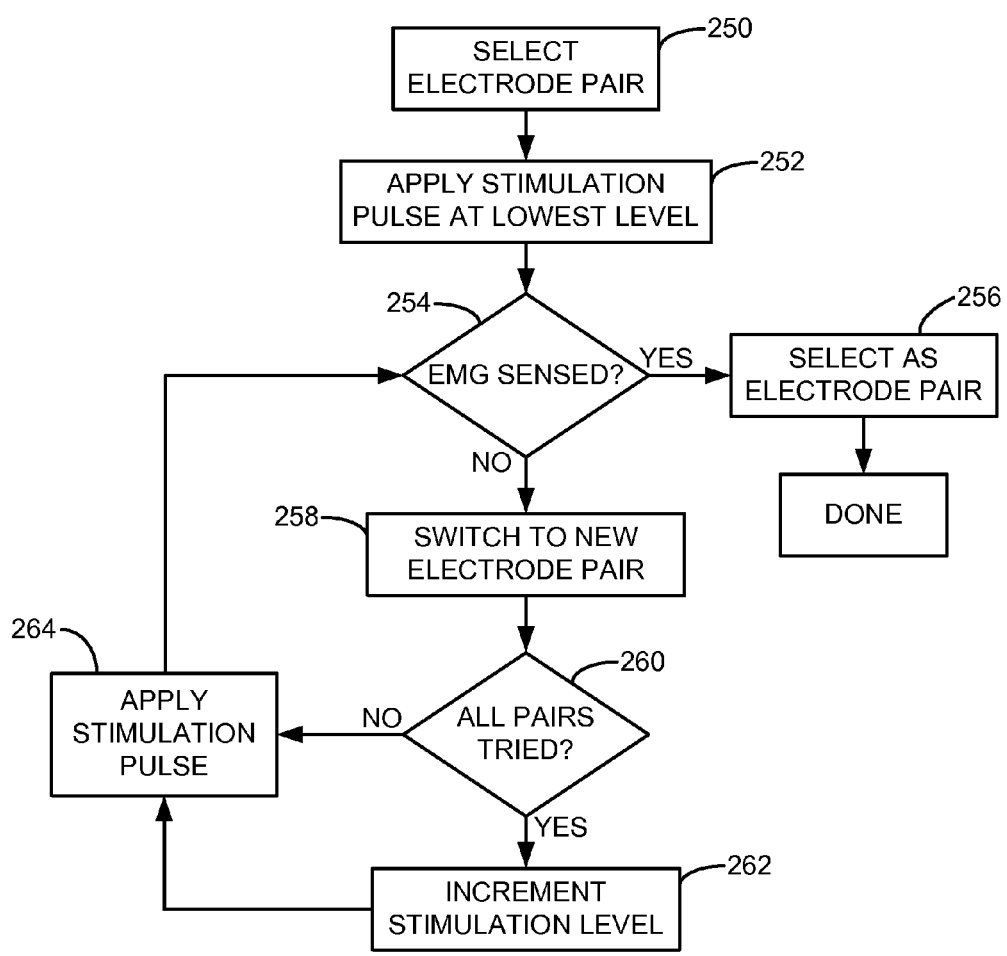

FIGS. 7 and 8 are flowcharts illustrating calibration routines for the device 100 in accordance with embodiments of the invention that may be performed using the controller 106. The calibration routines are similar to that described above with regard to FIG. 5, except that they generally begin at a minimum pulse power level or a low power level setting rather than a high power level setting. This may provide the patient with greater comfort due to the lower power of the initial stimulation pulse.

With reference to FIG. 7, candidate stimulation therapy settings are initially designated using the controller 126 that include an identification of a candidate pair of the electrodes 106, as indicated at 220, which are enabled by the controller 126 through the closing of one or more of the switches 130. At 222, a stimulation pulse is applied at a minimum or other preset low power level based on a candidate stimulation pulse parameter. At 224, the EMG response from the patient is sensed, such as using the sensing circuit 140, and the output signal produced by the sensing circuit 140 is analyzed by the controller 126. If the controller 126 determines that the output signal 144 indicates that a sufficient EMG response was generated by the patient at step 224, the calibration routine moves to 226 where the controller 126 sets the stimulation therapy settings to identify the candidate pair of electrodes 106 as the pair of electrodes through which stimulation pulses are to be delivered during subsequent stimulation therapies, and the current pulse power level as the power level of the stimulation pulses to be generated by the stimulation circuit 104 during subsequent stimulation therapies, thereby completing the calibration routine.

If the controller 126 determines that an EMG response from the patient is not sensed or does not meet a threshold requirement at 224, the candidate settings are adjusted by incrementing the stimulation pulse power level by one unit, at 228, and a stimulation pulse at the new pulse power level is applied to the patient through the candidate pair of the electrodes 106, at 229. At 230, the controller 126 determines whether the output signal 144 from the sensing circuit 140 indicates that an EMG signal produced by the patient in response to the stimulation pulse is sensed by the device 100. If the EMG signal is not sensed or is insufficient, the method moves back to 228 and the candidate stimulation pulse power level is incremented and another stimulation pulse is applied to the patient through the candidate pair of electrodes 106, at 229, until a sufficient EMG is sensed at 230. If the controller 126 determines that a sufficient EMG signal is sensed by the device 100 at 230, the controller 126 designates the current pair of electrodes 106 and the current stimulation pulse power as final candidate stimulation settings, at 232.

This process is generally repeated for a plurality of the available pairs of electrodes 106 to determine which pairs of the electrodes produce a sufficient EMG response with the lowest pulse power. Thus, at 234, a new candidate pair of electrodes 106 is selected. The final candidate stimulation pulse power level is decreased by one unit and a stimulation pulse is applied to the patient through the candidate pair of electrodes 106, at 238. If the controller 126 determines that a sufficient EMG signal is not sensed by the device 100 at 240, the stimulation power level is increased by one unit (i.e., returns to the final candidate stimulation pulse power level), at 242, and a new candidate pair of electrodes 106 is selected at 234 for testing.

If the controller 126 determines that a sufficient EMG signal is sensed at 240, the candidate pair of electrodes 106 is designated as the new final candidate pair of electrodes 106, and the current pulse power or stimulation level set at 238 is designated as the final candidate pulse power, at 244. The method then continues by returning to 238. Once the EMG signal is no longer sensed at 240, the method continues by moving to 242.

If all of the pairs of electrodes 106 have been tested at 234, the final stimulation therapy settings are set to the current final candidate stimulation settings and the calibration routine is completed, as indicated at 236.

The calibration routine illustrated in FIG. 8 differs from the calibration routine illustrated in FIG. 7 by checking a stimulation power level for all or a group of the available electrodes 106 before increasing the power level. Candidate stimulation therapy settings are initially designated using the controller 126 that include an identification of a candidate pair of the electrodes 106, as indicated at 250, which are enabled by the controller 126 through the closing of one or more of the switches 130. At 252, a stimulation pulse is applied at a minimum or other preset low power level based on a candidate stimulation pulse parameter. At 254, the EMG response from the patient is sensed, such as using the sensing circuit 140, and the output signal produced by the sensing circuit 140 is analyzed by the controller 126. If the controller 126 determines that the output signal 144 indicates that a sufficient EMG response was generated by the patient at step 254, the calibration routine moves to 256 where the controller 126 sets the stimulation therapy settings to identify the candidate pair of electrodes 106 as the pair of electrodes through which stimulation pulses are to be delivered during subsequent stimulation therapies, and the current pulse power level as the power level of the stimulation pulses to be generated by the stimulation circuit 104 during subsequent stimulation therapies, thereby completing the calibration routine.

If the controller 126 determines that an EMG response from the patient is not sensed or does not meet a threshold requirement at 254, the candidate settings are adjusted by selecting another candidate pair of electrodes 106, at 258. At 260, the controller 126 determines whether all of the candidate electrode pairs have been tested at the current candidate pulse power level. If all of the candidate electrode pairs have not been tested, a stimulation pulse in accordance with the current candidate pulse power is applied to the patient through the current candidate pair of electrodes 106, at 264, and the method returns to 254 where the controller 126 determines if a sufficient EMG signal is detected by the sensing circuit 140, as discussed above. If all of the candidate electrode pairs have been tested, the candidate pulse power level is incremented by one unit, at 262, and a stimulation pulse is applied to the patient through the current candidate electrode pair, at 264, and the method returns to 254. In this manner, the stimulation therapy settings for the device 100 are set to designate the pair of electrodes 106 through which a stimulation pulse having the lowest pulse power may be applied to the patient to effectively stimulate the tibial nerve 112 and treat the pelvic condition.

Applicable embodiments described above with regard to FIG. 5 may be applied to the calibration routine illustrated in FIG. 7. In some embodiments, the calibration routine increases the final pulse power level setting of the stimulation pulses by one unit to provide a safety margin.

Although the present invention has been described with reference to preferred embodiments, workers skilled in the art will recognize that changes may be made in form and detail without departing from the spirit and scope of the invention.

What is claimed is:

1. A tibial nerve stimulation therapy device configured to provide an electrical stimulation therapy to branches of the tibial nerve of a patient, the device comprising:
   a plurality of stimulation electrodes;
   a support member configured to support the plurality of electrodes on a top surface of an ankle area of the patient;
   a stimulation circuit configured to generate electrical stimulation pulses;
   a sensing circuit configured to generate an output signal indicative of an electromyogram (EMG) signal generated by the patient; and
   a controller comprising a processor, the controller configured to:
      execute a plurality of unique stimulation therapies, during which an electrical stimulation pulse is delivered through a pair of the electrodes, each stimulation therapy performed in accordance with unique stimulation therapy settings;
      analyze the output signals generated by the sensing circuit in response to each of the stimulation therapies; and
      designate final stimulation therapy settings based on the analyzed output signals;
   wherein the stimulation therapy settings include at least one of an identification of a pair of the electrodes through which the electrical stimulation pulses are delivered during a stimulation therapy, and at least one parameter defining the electrical stimulation pulses generated by the stimulation circuit.

2. The device according to claim 1, wherein the stimulation circuit comprises:
   a power supply;
   a transformer having a primary winding and a secondary winding, wherein the power supply is connected in series with the primary winding; and
   a pulse control switch connected in series with the power supply and the primary winding;

wherein the controller is configured to open and close the pulse control switch to generate the stimulation pulses in the secondary winding.

3. The device according to claim 2, further comprising a plurality of pulse routing switches each in series between one of the electrodes and the secondary winding, wherein the controller is configured to selectively open or close each of the pulse routing switches to route the electrical stimulation pulses to the identified pair of electrodes.

4. The device according to claim 1, further comprising a plurality of pulse routing switches each connected in series with one of the stimulation electrodes, wherein the controller is configured to selectively open or close each of the pulse routing switches to route the electrical stimulation pulses to the identified pair of electrodes.

5. The device according to claim 1, wherein the sensing circuit comprises an amplifier coupled to a sense electrode, wherein an EMG signal is sensed through the sense electrode and the amplifier produces the output signal.

6. The device according to claim 5, wherein the sense electrode is one of the plurality of stimulation electrodes.

7. The device according to claim 1, wherein the stimulation therapy settings include an identification of a pair of the stimulation electrodes through which the electrical stimulation pulses are delivered during a stimulation therapy.

8. The device according to claim 7, wherein the stimulation therapy settings include at least one parameter defining the electrical stimulation pulses generated by the stimulation circuit.

9. The device according to claim 8, wherein the at least one parameter includes a power level, which designates a power level of the electrical stimulation pulses generated by the stimulation circuit.

10. A method of calibrating a tibial nerve stimulation therapy device, which includes a plurality of stimulation electrodes, a stimulation circuit, a sensing circuit, and a controller comprising a processor, the method comprising steps of:
performing multiple unique stimulation therapies on a patient using the device, each stimulation therapy comprising steps of:
generating an electrical stimulation pulse using the stimulation circuit;
delivering the electrical stimulation pulse to the tibial nerve of the patient through a candidate pair of the stimulation electrodes; and
sensing an electromyogram (EMG) signal generated by the patient in response to the delivering step, and generating an output signal indicative of the EMG signal, using the sensing circuit;
analyzing the output signals generated by the sensing circuit using the controller; and
designating the stimulation therapy settings for subsequent stimulation therapies based on the analyzing step, using the controller.

11. The method according to claim 10, wherein the performing step comprises steps of:
designating candidate settings using the controller, the candidate settings including an identification of a candidate pair of the electrodes, and at least one candidate stimulation pulse parameter;
performing a tibial nerve stimulation therapy on a patient comprising steps of:
(i) generating an electrical stimulation pulse in accordance with the at least one candidate stimulation pulse parameter using the stimulation circuit;
(ii) delivering the electrical stimulation pulse to the tibial nerve of the patient through the candidate pair of the electrodes; and
(iii) sensing an EMG signal generated by the patient in response to the delivering step (ii), and generating an output signal indicative of the EMG signal, using the sensing circuit;
adjusting the candidate settings using the controller; and
repeating performing a tibial nerve stimulation therapy and the adjusting step a limited number of times.

12. The method according to claim 11, wherein the adjusting step comprises changing the candidate pair of the electrodes in the candidate settings using the controller.

13. The method according to claim 11, wherein the adjusting step comprises adjusting the at least one candidate stimulation pulse parameter of the candidate settings using the controller.

14. The method according to claim 13, wherein:
the at least one candidate stimulation pulse parameter includes a power level, which designates a power level of the electrical stimulation pulses generated by the stimulation circuit; and
the adjusting step comprises adjusting the power level of the candidate settings using the controller.

15. The method according to claim 14, wherein adjusting the power level comprises increasing the power level.

16. The method according to claim 15, wherein the repeating step comprises repeating performing a tibial nerve stimulation therapy and the adjusting step until the output signal indicates that an EMG signal has been sensed by the sensing circuit.

17. The method according to claim 14, wherein adjusting the power level comprises decreasing the power level.

18. The method according to claim 17, wherein the repeating step comprises repeating performing a tibial nerve stimulation therapy and the adjusting step until the output signal indicates that an EMG signal has not been sensed by the sensing circuit.

19. The method according to claim 11, wherein the adjusting step comprises:
increasing the power level when the output signal indicates that an EMG signal was not sensed by the sensing circuit; and
decreasing the power level when the output signal indicates that an EMG signal was sensed by the sensing circuit.

\* \* \* \* \*